(12) United States Patent
Clarke et al.

(10) Patent No.: US 10,322,265 B2
(45) Date of Patent: Jun. 18, 2019

(54) APPARATUS AND METHOD FOR ACCESSING AN EPIDURAL SPACE

(71) Applicants: Mark Leeroy Clarke, Fulton, MD (US); Shuichi Amano, Bethlehem, PA (US); Michael Creighton, Warrington, PA (US)

(72) Inventors: Mark Leeroy Clarke, Fulton, MD (US); Shuichi Amano, Bethlehem, PA (US); Michael Creighton, Warrington, PA (US)

( * ) Notice: Subject to any disclaimer, the term of this patent is extended or adjusted under 35 U.S.C. 154(b) by 0 days.

(21) Appl. No.: 15/638,777

(22) Filed: Jun. 30, 2017

(65) Prior Publication Data

US 2018/0098786 A1    Apr. 12, 2018

Related U.S. Application Data

(60) Provisional application No. 62/407,069, filed on Oct. 12, 2016.

(51) Int. Cl.
*A61M 25/06* (2006.01)
*A61B 17/34* (2006.01)
(Continued)

(52) U.S. Cl.
CPC .......... *A61M 25/065* (2013.01); *A61B 17/34* (2013.01); *A61B 17/3401* (2013.01); *A61B 17/3415* (2013.01); *A61M 5/158* (2013.01); *A61M 25/06* (2013.01); *A61B 17/3496* (2013.01); *A61B 2017/0046* (2013.01); *A61B 2017/00469* (2013.01); *A61B 2090/0811* (2016.02); *A61M 2005/1585* (2013.01); *A61M 2005/1586* (2013.01); *A61M 2025/0007* (2013.01);
(Continued)

(58) Field of Classification Search
CPC .......... A61M 5/158; A61M 2005/1585; A61M 2005/1586; A61M 2025/0007; A61M 2025/0175; A61M 25/06; A61M 25/0637; A61M 25/065; A61M 2210/1003; A61B 2017/0046; A61B 2017/00469; A61B 17/34; A61B 17/3401; A61B 17/3415; A61B 17/3496
See application file for complete search history.

(56) References Cited

U.S. PATENT DOCUMENTS 4,958,901 A * 9/1990 Coombs ............. A61B 17/3401
264/145
5,163,901 A * 11/1992 Eldor ................. A61B 17/3401
604/158
(Continued)

*Primary Examiner* — Shefali D Patel
(74) *Attorney, Agent, or Firm* — Dunlap Bennett & Ludwig PLLC

(57) ABSTRACT

An apparatus for locating and accessing an epidural space within a patient. The apparatus includes a handle having a top end and a bottom end. A handle channel is formed through the handle running from the top end to the bottom end. A proximal end of a hollow needle extends from the bottom end of the handle and aligns with the handle channel. A distal end of the hollow needle is sharp and pointed. An obturator is disposed within the hollow needle and the handle channel. A distal end of the obturator is rounded and blunt and extends from the distal end of the hollow needle. A proximal end of the obturator extends beyond the handle channel at the top end of the handle.

9 Claims, 4 Drawing Sheets

(51) Int. Cl.
*A61M 5/158* (2006.01)
*A61M 25/00* (2006.01)
*A61M 25/01* (2006.01)
*A61B 17/00* (2006.01)
*A61B 90/00* (2016.01)

(52) U.S. Cl.
CPC .............. *A61M 2025/0175* (2013.01); *A61M 2210/1003* (2013.01)

(56) References Cited

U.S. PATENT DOCUMENTS 5,637,096 A * 6/1997 Yoon ............... A61B 10/06
604/158
2003/0114797 A1* 6/2003 Vaillancourt ....... A61M 5/3213
604/171

\* cited by examiner

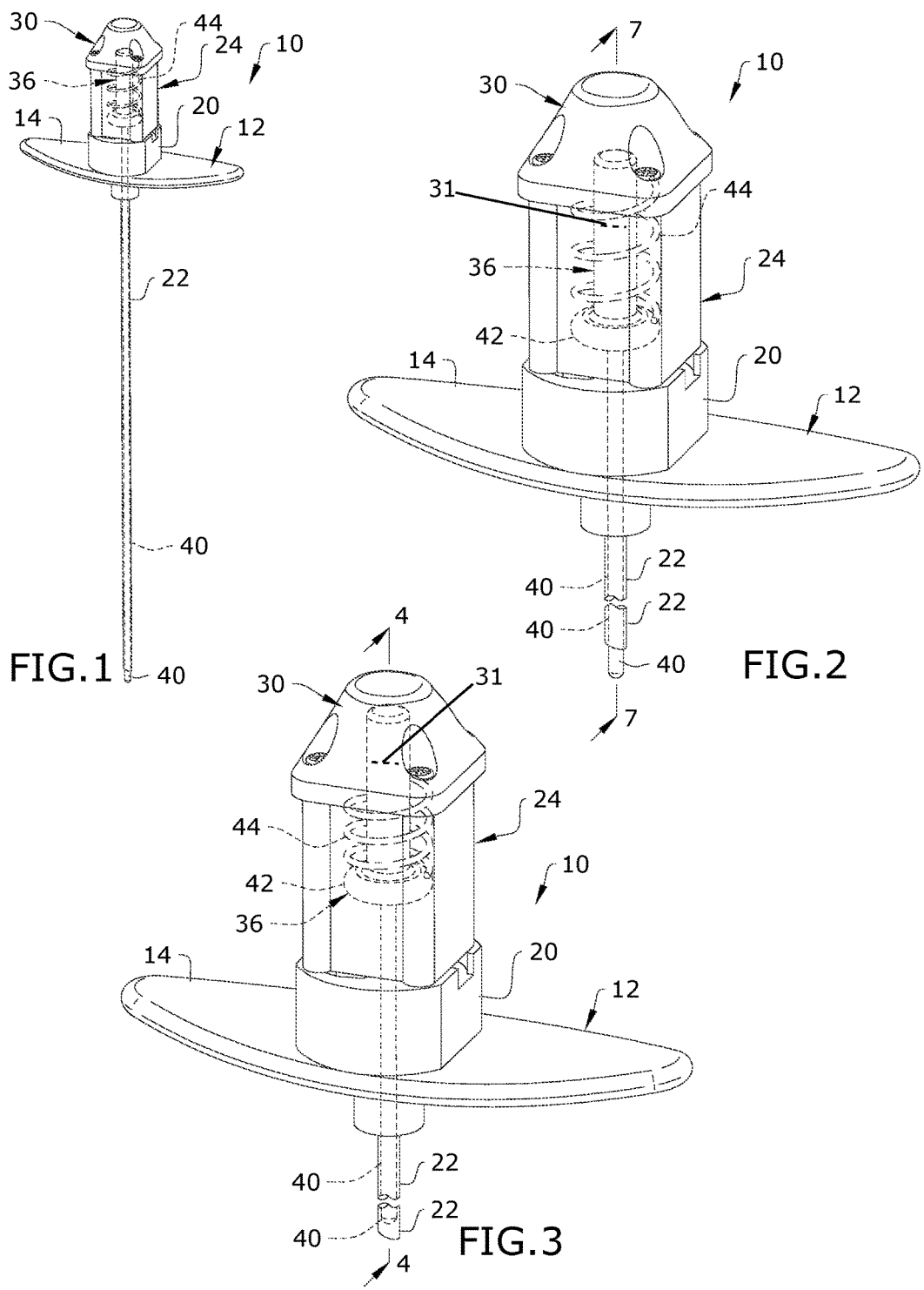

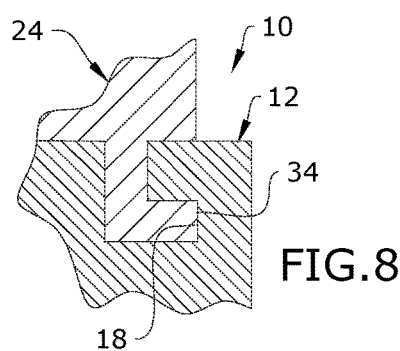
FIG.8
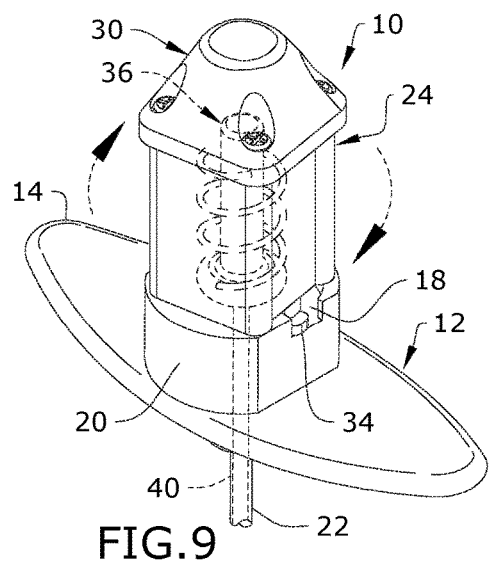
FIG.9
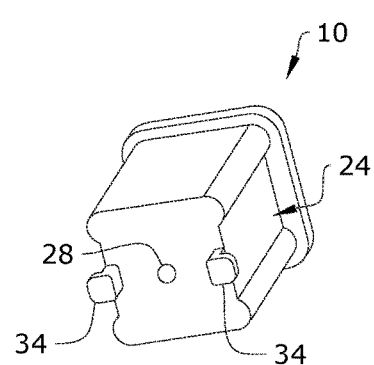
FIG.11
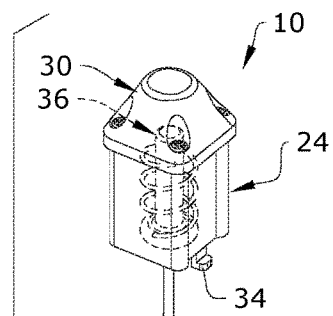
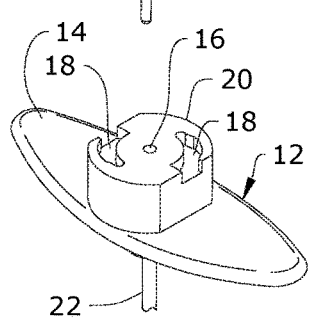
FIG.10

APPARATUS AND METHOD FOR ACCESSING AN EPIDURAL SPACE

CROSS-REFERENCE TO RELATED APPLICATION

This application claims the benefit of priority of U.S. provisional application No. 62/407,069, filed Oct. 12, 2016, the contents of which are herein incorporated by reference.

BACKGROUND OF THE INVENTION

The present invention relates to administering epidurals and, more particularly, to an apparatus and method for accessing an epidural space.

Epidural administration is a medical route of administration in which a drug or contrast agent is injected into the epidural space of the spinal column. Techniques such as epidural analgesia and epidural anesthesia employ this route of administration. The epidural route is frequently employed by certain physicians and nurse anesthetists to administer diagnostic and therapeutic chemical substances, as well as certain analgesic and local anesthetic agents. Epidural techniques frequently involve injection of drugs through a catheter placed into the epidural space. The injection can result in a loss of sensation by blocking the transmission of signals through nerve fibers in or near the spinal column.

Current epidural needles have a higher risk of dural puncture. They are also less reliable when used for combined epidural spinal techniques. Current needles use loss of resistance or hanging drop techniques which depend on stepwise advance and can easily be inadvertently advanced into the subdural space, especially in the hands of inexperienced practitioners. The use of air or saline syringes are cumbersome and also represent additional risk. The curved epidural Huber tip needles can deflect spinal needles when used in a combined technique.

As can be seen, there is a need for an improved apparatus and method for locating the epidural space.

SUMMARY OF THE INVENTION

In one aspect of the present invention, an apparatus for accessing an epidural space comprises: a handle comprising a top end and a bottom end and forming a channel therethrough; a hollow needle comprising a proximal end and a distal end, wherein the proximal end extends from the bottom end of the handle and is aligned with the channel, and the distal end comprises a pointed tip; and an obturator disposed within the hollow needle and the channel of the handle, wherein the obturator comprises a proximal end and a distal end, wherein the distal end is blunt and is extending beyond the distal end of the needle, and the proximal end is extending beyond the channel at the top end of the handle.

In another aspect of the present invention, a method of accessing an epidural space comprises the steps of: providing an apparatus comprising: a hollow needle comprising a proximal end and a distal end comprising a pointed tip; and an obturator disposed within the hollow needle, wherein the obturator comprises a proximal end and a distal end, wherein the distal end is blunt and is biased to extend beyond the distal end of the hollow needle, and the proximal end is extending beyond the proximal end of the hollow needle; piercing tissue with the pointed tip of the needle, wherein the distal end of obturator recedes into the needle against the bias; and reaching an epidural space with the needle, wherein the distal end is biased back to extend beyond the distal end of the needle due to a lack of tissue within the epidural space.

These and other features, aspects and advantages of the present invention will become better understood with reference to the following drawings, description and claims.

BRIEF DESCRIPTION OF THE DRAWINGS

FIG. 1 is a perspective view of an embodiment of the present invention;

FIG. 2 is a detail truncated perspective view of the present invention shown in an exemplary deployed position FIG. 3 is a detail truncated perspective view of the present invention shown in an exemplary recessed position;

FIG. 8 is a section detail view of the present invention taken along line 8-8 in FIG. 7;

FIG. 9 is a detail perspective view of an embodiment of the present invention;

FIG. 10 is an exploded view of an embodiment of the present invention;

FIG. 11 is a bottom perspective view of an embodiment of the present invention;

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Figure 4:
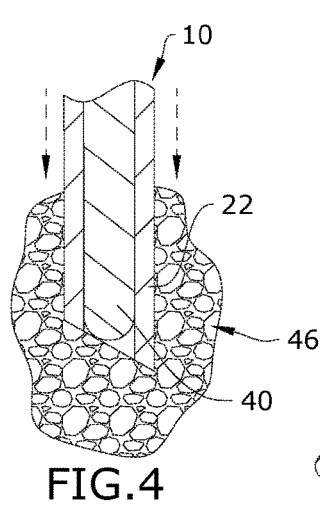
FIG. 4 is a section detail view illustrating a needle of the present invention entering tissue with an obturator recessed within the needle.
Figure 5:
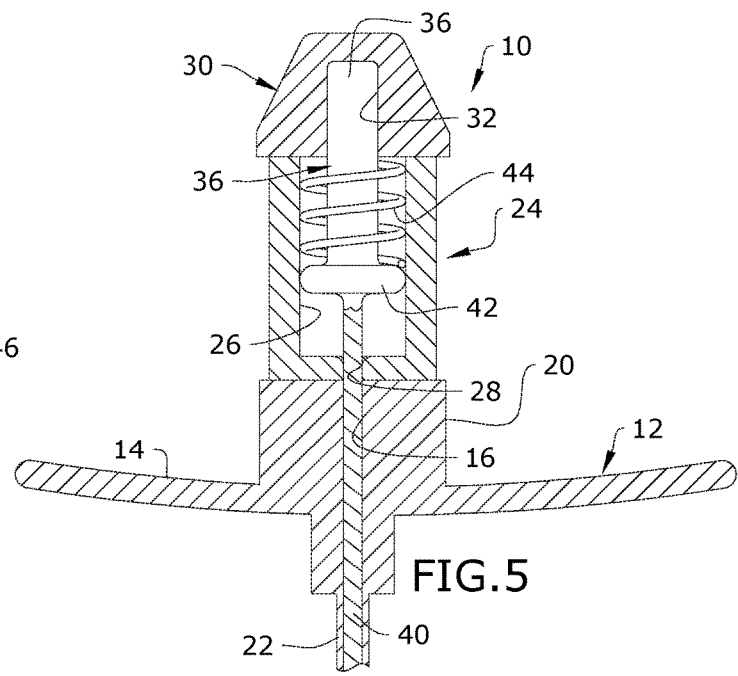
FIG. 5 is a section detail view of the present invention taken along line 4-4 in FIG. 3.
Figure 6:
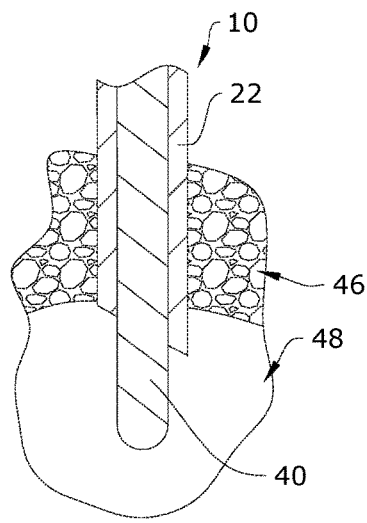
FIG. 6 is a section detail view illustrating a needle of the present invention entering epidural space with an obturator extending from the needle.
Figure 7:
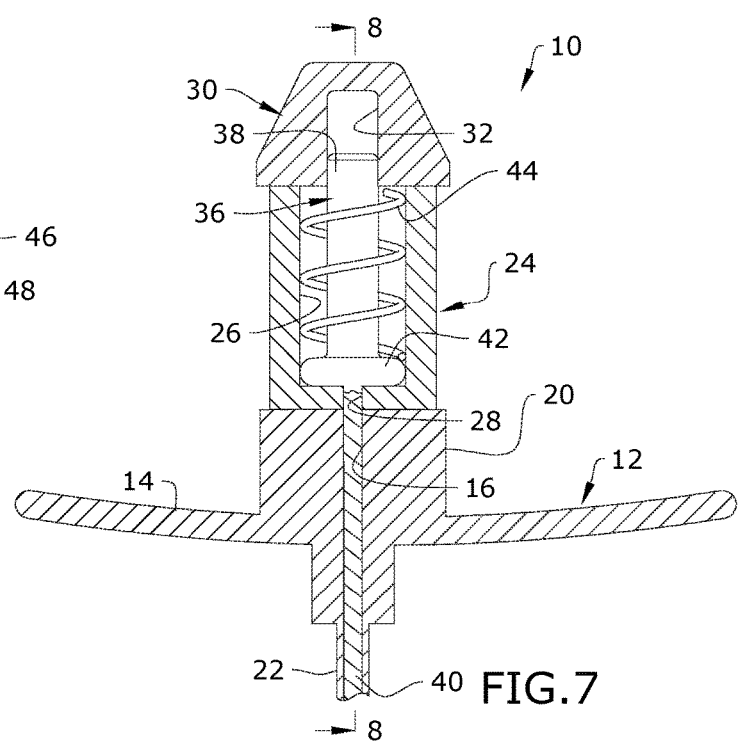
FIG. 7 is a section detail view of the present invention taken along line 7-7 in FIG. 2.

Referring to FIGS. 1 through 11, the present invention includes an apparatus 10 for locating and accessing an epidural space 48 within a patient. The apparatus 10 includes a handle 12 having a top end and a bottom end. A handle channel 16 is formed through the handle 12 running from the top end to the bottom end. A proximal end of a hollow needle 22 extends from the bottom end of the handle 12 and aligns with the handle channel 16. A distal end of the hollow needle 22 is sharp and pointed. An obturator 36 is disposed within the hollow needle 22 and the handle channel 16. A distal end of the obturator 36 is rounded and blunt and extends from the distal end of the hollow needle 22. A proximal end of the obturator 36 extends beyond the handle channel 16 at the top end of the handle 12.

The hollow needle 22 may be made of an elongated hollow tube of a rigid material, such as metal. As mentioned above, the distal end of the hollow needle 22 is sharp and pointed to easily pierce the skin and tissue 46 of the patient. In certain embodiments, the sharp and pointed end may be beveled.

The obturator 36 may include an elongated shaft 40 that fits within the hollow needle 22. The obturator 36 may be made of a soft flexible material, such as a polymer. The polymer may be plastic, biocompatible polyethylene, polytetrafluoroethylene, polycarbonate and the like. The obturator 36 may further include a stopper 42 at the proximal end. The stopper 42 has larger diameter than the handle channel 16 preventing the proximal end of the obturator 36 from entering the handle channel 16 and the hollow needle 22. In certain embodiments, a shaft 38 upwardly extends from the stopper 42.

The handle 12 of the present invention is used to manipulate the hollow needle 22 to accurately pierce a user's tissue 46. The handle 12 may include a platform 14 having laterally extending arms. A top protrusion 20 may extend upwardly from a top surface of the platform 14. A bottom protrusion may extend downwardly from the bottom surface of the platform 14. The handle channel 16 runs through the top protrusion 20, the platform 14 and the bottom protrusion.

The present invention may further include an obturator housing 24. The stopper 42 and the shaft 38 may be disposed within the obturator housing 24. The obturator housing 24 may quickly connect and disconnect with the handle 12 so that the obturator 36 may be quickly removed once the epidural space 40 is located. The obturator housing 24 may include a top end and a bottom end. The bottom end includes a housing channel 28 aligned with the handle channel 16. An internal cavity 26 is formed in between the top end and the bottom end. The stopper and shaft 38 are disposed within the internal cavity 26. The obturator 36 runs through the housing channel 28 and into the handle channel 16.

The distal end of the obturator 36 is biased to extend beyond the distal end of the hollow needle 22. When the distal end of the obturator 36 is pressed against tissue 46, the obturator 36 recesses into the hollow needle 22 and the hollow needle 22 pierces the tissue 46. Once the hollow needle 22 reaches the epidural space 48, the distal end of the obturator 36 biases back to the extended position, indicating to the user that the hollow needle 22 has reached the epidural space 48.

The apparatus 10 includes an automatic recessed and protruding mechanism. In such embodiments, a spring 44 is disposed around the shaft 38. The spring 44 abuts against the stopper 42 and is disposed in between the stopper 42 and the top end of the obturator housing 24. A gap 32 is formed at the top end of the obturator housing 24 in which a top end of the shaft 38 fits within. The spring 44 biases the distal end of the obturator 36 out of the distal end of the hollow needle 22. When the distal end of the obturator 36 presses against the tissue 46, the obturator 36 is pushed upwards so that the shaft 38 enters the gap 32 and the distal end recesses within the hollow needle 22.

In certain embodiments, a colored strip 31 may be printed on the shaft 38 and a portion of the obturator housing 24 is made of a transparent material. The colored strip 31 is positioned to disappear when the shaft 38 is disposed within the gap 32. The colored strip 31 is revealed through the transparent material when the shaft 38 biases out of the gap 32. Therefore, the user is easily able to determine when the end of the hollow needle has entered the epidural space 48.

As mentioned above, the obturator housing 24 is attached to the handle 12 by a quick connect and disconnect. In such embodiments, a locking slot 18 may be formed on the top of the top protrusion 20 of the handle 12. Locking lets 34 may extend downwardly from the bottom end of the obturator housing 24. The user may engage the legs 34 into the locking slot 18 to attach the obturator housing 24 to the handle 12 and disengage the locking legs 34 from the locking slot 18 to remove the obturator housing 24 from the handle 12. In certain embodiments, the slot 18 may include a first and second curved slots. The curved slots may include an enlarged entrance and a narrow engagement area having a lip. In such embodiments, the locking legs 34 may also include a lip. The locking legs 34 may enter the enlarged entrance and the obturator housing 24 may be rotated so that the lip of the locking legs 34 is disposed underneath the lip of the narrow engagement area of the slots 18, thereby locking the obturator housing 24 to the handle 12.

A method of using the present invention may include the following steps: providing the apparatus 10 mentioned above and grasping the handle 14; piercing tissue 46 with the pointed tip of the hollow needle 22, wherein distal end of obturator 36 recedes into the hollow needle 22 against the bias of the spring 44; reaching an epidural space 48 with the hollow needle 22, wherein the distal end of the obturator 36 is biased back to extend beyond the distal end of the hollow needle 12 due to a lack of tissue within the epidural space 48; detaching the obturator housing 24 from the handle 14; removing the obturator 40 from the hollow needle 22; inserting a catheter through the hollow needle 22 and into the epidural space 48; and delivering a medication through the catheter and into the epidural space 48.

Figure 12:
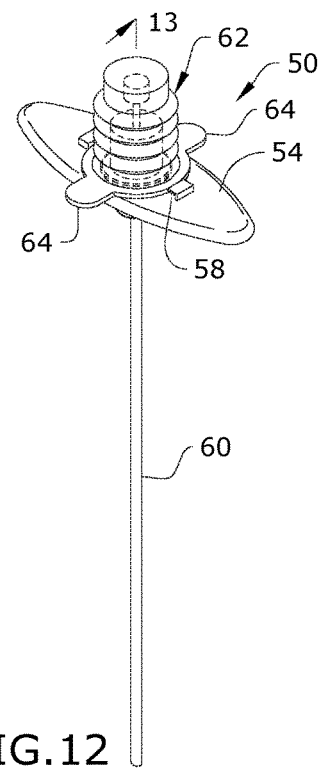
FIG. 12 is a perspective view of an embodiment of the present invention.
Figure 13:
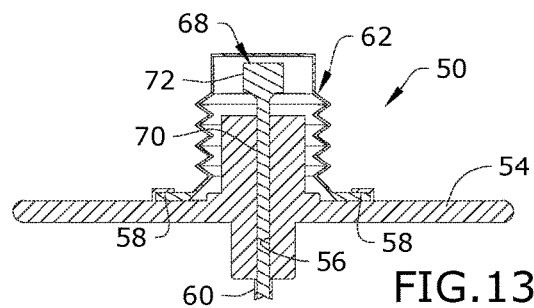
FIG. 13 is a section detail view of the present invention taken along line 13-13 in FIG. 12.
Figure 14:
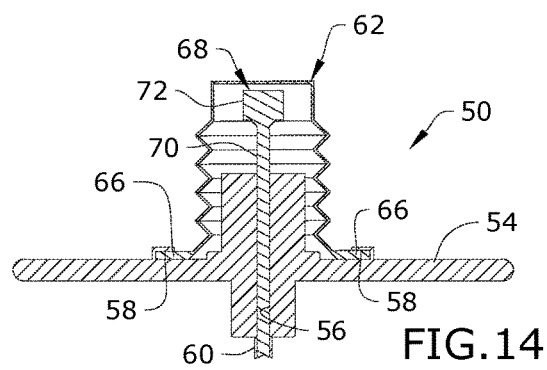
FIG. 14 is a section detail view of the present invention shown in a recessed configuration.
Figure 15:
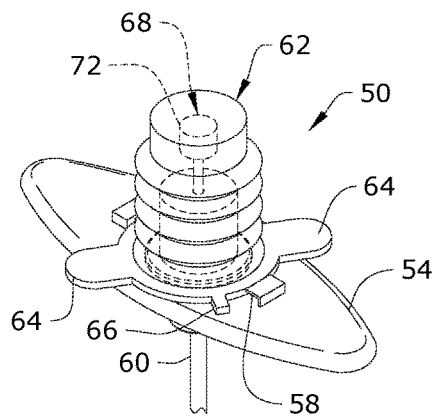
FIG. 15 is a detail perspective view of an embodiment of the present invention.
Figure 16:
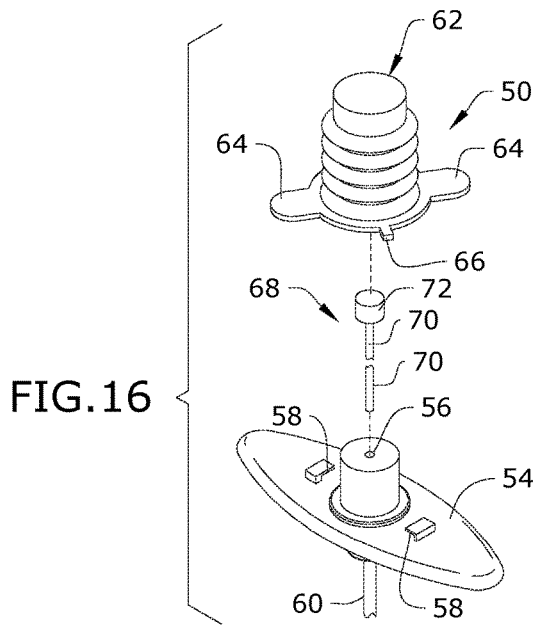
FIG. 16 is a detail exploded view of an embodiment of the present invention.

Referring to FIGS. 12 through 16, the present invention includes an apparatus 50 for locating and accessing an epidural space within a patient. The apparatus 50 includes a handle 52 having a top end and a bottom end. A handle channel 56 is formed through the handle 52 running from the top end to the bottom end. A proximal end of a hollow needle 60 extends from the bottom end of the handle 52 and aligns with the handle channel 56. A distal end of the hollow needle 60 is sharp and pointed. An obturator 68 is disposed within the hollow needle 60 and the handle channel 56. A distal end of the obturator 68 is rounded and blunt and extends from the distal end of the hollow needle 60. A proximal end of the obturator 68 extends beyond the handle channel 56 at the top end of the handle 52.

The obturator 68 includes a stopper 72 at the proximal end. The stopper 72 has larger diameter than the handle channel 56 preventing the proximal end of the obturator 68 from entering the handle channel 56 and the hollow needle 60.

The handle 52 of the present invention is used to manipulate the hollow needle 60 to accurately pierce a user's tissue. The handle 52 may include a platform 54 having laterally extending arms. A top protrusion may extend upwardly from a top surface of the platform 54. A bottom protrusion may extend downwardly from the bottom surface of the platform 54. The handle channel 16 runs through the top protrusion, the platform 54 and the bottom protrusion.

The apparatus 50 includes a manual recessed and protruding mechanism. In such embodiments, the present invention includes an accordion sleeve 62 having a closed top end and an open bottom end leading into an internal cavity. The open bottom end is releasably attached to the top end of the handle 54 so that the stopper 72 is disposed within the internal cavity. When in use, the user may gently press against the closed top end of the accordion sleeve 62 and thereby gently press against the stopper 72 with their thumb or other finger. The user may pierce the tissue, which pushes the obturator 68 upwards into the needle 60. The stopper 72 is pushed against the user's thumb and the accordion sleeve 62 extends to a stretched position. When the user reaches the epidural space, the user is easily able to push the obturator 68 back outwards beyond the distal end of the hollow needle 60, indicating to the user that the distal end of the hollow needle 60 is within the epidural space.

As mentioned above, the accordion sleeve 62 is attached to the handle 54 by a quick connect and disconnect. In such embodiments, a locking clots 58 are formed on a top surface of the platform 54. Laterally protruding tabs 48 extend from the open bottom end of the accordion sleeve 62. A user may simply place the open bottom end onto the top surface and rotate the protruding tabs 48 to be underneath the locking slots 58 to attach the accordion sleeve 62 to the handle 54. To disconnect the accordion sleeve 62, the accordion sleeve 62 may be rotated so that the protruding tabs 48 are no longer disposed underneath the locking slots 58 and the accordion sleeve 62 may be removed from the handle 52. The open bottom end of the accordion sleeve 62 may further include grips 64 extending laterally so that user's may easily attach and detach the accordion sleeve 62 to the handle 54.

It should be understood, of course, that the foregoing relates to exemplary embodiments of the invention and that modifications may be made without departing from the spirit and scope of the invention as set forth in the following claims.

What is claimed is:

1. An apparatus for accessing an epidural space comprising:
   a handle comprising a top end and a bottom end and forming a handle channel therethrough;
   a hollow needle comprising a proximal end and a distal end, wherein the proximal end extends from the bottom end of the handle and is aligned with the handle channel, and the distal end comprises a pointed tip;
   an obturator disposed within the hollow needle and the handle channel of the handle, wherein the obturator comprises a proximal end and a distal end, wherein the distal end of the obturator is blunt and is extending beyond the distal end of the needle, and the proximal end of the obturator is extending beyond the handle channel at the top end of the handle and comprises a stopper having a larger diameter than the handle channel; and
   an obturator housing releasably attachable to the top end of the handle, wherein the obturator housing comprises a top end, a bottom end comprising a housing channel aligned with the handle channel, and an internal cavity disposed therebetween the top end of the obturator housing and the bottom end of the obturator housing, wherein the stopper is disposed within the internal cavity and the obturator runs through the housing channel and into the handle channel.

2. The apparatus of claim 1, wherein the hollow needle is made of a rigid material and the obturator is made of a flexible material.

3. The apparatus of claim 1, wherein the handle comprises a platform comprising laterally extending arms.

4. The apparatus of claim 1, further comprising a spring disposed around a shaft upwardly extending from the stopper, wherein the spring biases the distal end of the obturator beyond the distal end of the hollow needle, and a gap is formed in between a top end of the shaft and the top end of the obturator housing.

5. The apparatus of claim 4, further comprising a strip printed on the shaft, wherein the strip is positioned to disappear when the shaft is disposed within the gap and the strip is revealed when the shaft biases out of the gap.

6. The apparatus of claim 1, wherein the obturator housing comprises locking protrusions extending from the bottom end of the obturator housing that releasably lock into slots formed on the top end of the handle.

7. A method of accessing an epidural space comprising the steps of:
   (a) providing an apparatus comprising:
      a handle comprising a top end and a bottom end and forming a handle channel therethrough;
      a hollow needle comprising a proximal end and a distal end, wherein the proximal end extends from the bottom end of the handle and is aligned with the handle channel, and the distal end comprises a pointed tip;
      an obturator disposed within the hollow needle and the handle channel of the handle, wherein the obturator comprises a proximal end and a distal end, wherein the distal end of the obturator is blunt and is extending beyond the distal end of the hollow needle, and the proximal end of the obturator is extending beyond the handle channel at the top end of the handle and comprises a stopper having a larger diameter than the handle channel; and
      an obturator housing releasably attachable to the top end of the handle, wherein the obturator housing comprises a top end, a bottom end comprising a housing channel aligned with the handle channel, and an internal cavity disposed therebetween the top end of the obturator housing and the bottom end of the obturator housing, wherein the stopper is disposed within the internal cavity and the obturator runs through the housing channel and into the handle channel;
   (b) piercing tissue with the pointed tip of the needle, wherein the distal end of the obturator recedes into the needle against bias; and
   (c) reaching the epidural space with the needle, wherein the distal end of the obturator extends beyond the distal end of the needle due to a lack of tissue within the epidural space.

8. The method of claim 7, further comprising the step of:
   (d) removing the obturator housing from the handle.

9. The method of claim 8, further comprising the steps of:
   (e) removing the obturator from the needle after step (d); and
   (f) inserting a catheter through the needle and into the epidural space.

* * * * *